US006255065B1

(12) United States Patent
Errington

(10) Patent No.: US 6,255,065 B1
(45) Date of Patent: Jul. 3, 2001

(54) BACILLUS STRAIN AND ANTIBIOTIC SCREENING METHOD

(75) Inventor: Jeffery Errington, Oxford (GB)

(73) Assignee: ISIS Innovation Limited, Oxford (GB)

( * ) Notice: Subject to any disclaimer, the term of this patent is extended or adjusted under 35 U.S.C. 154(b) by 0 days.

(21) Appl. No.: 09/319,778

(22) PCT Filed: Dec. 11, 1997

(86) PCT No.: PCT/GB97/03414

§ 371 Date: Jun. 11, 1999

§ 102(e) Date: Jun. 11, 1999

(87) PCT Pub. No.: WO98/26088

PCT Pub. Date: Jun. 18, 1998

(30) Foreign Application Priority Data

Dec. 12, 1996 (GB) .................................................. 9625832

(51) Int. Cl.$^7$ ................................ C12H 1/21; C12Q 1/18
(52) U.S. Cl. ............................ 435/32; 435/4; 435/252.5; 435/252.31
(58) Field of Search .................. 435/32, 252.31, 435/252.5

(56) References Cited

FOREIGN PATENT DOCUMENTS 0 174 477  3/1986  (EP).
96/35804  11/1996  (WO).
97/00325   1/1997  (WO).

OTHER PUBLICATIONS

W. Haldenwang et al., "The sigma factors of *Bacillus subtilis*", Microbiological Reviews, vol. 59, No. 1, pp. 1–30, Mar. 1995.

D. Sun et al., "Effect of chromosome location of *Bacillus subtilis* forespore genes on their spo gene dependence and transcription by Eo$^{-F}$ : Identification of features of good Eo$^{-F}$–dependent promoters", Journal of Bacteriology, vol. 173, No. 24, pp. 7867–7874, Dec. 1991.

J. Errington et al., Determination of cell fate in *Bacillus subtilis*, vol. 12, No. 1, Reviews, pp. 31–34, Jan. 1996.

P. Stragier et al., "Processing of a sporulation sigma factor in *Bacillus subtilis*: How morphological structure could control gene expression", Cell, vol. 52, pp. 697–704, Mar. 11, 1988.

R. Passmore et al., "A companion to medical studies", General scope of chemotherapy, vol. 2, pp. 20.9–20.31, 1970.

Sussman et al. 1991 Cloning, nucleotide sequence, and regulation of the Bacillus subtilis gpr gene, which codes for the protease that initiates degradation of small, acid–soluble proteins during spore germination. Journal of Bacteriology. vol. 173 (1): 29.*

Lewin. 1990. Genes IV. Oxford University Press, p. 817.*

* cited by examiner

*Primary Examiner*—Mary E. Mosher
*Assistant Examiner*—Shanon Foley
(74) *Attorney, Agent, or Firm*—Wenderoth, Lind & Ponack, L.L.P.

(57) ABSTRACT

A Bacillus strain has a chromosome with two reporter genes, a first reporter gene having a promoter which is dependent on active $\sigma^F$ factor, and a second gene having a promoter regulated similarly to the gene encoding the sigma factor. A method of using Bacillus strain in an assay for screening putative antibiotics.

10 Claims, 2 Drawing Sheets

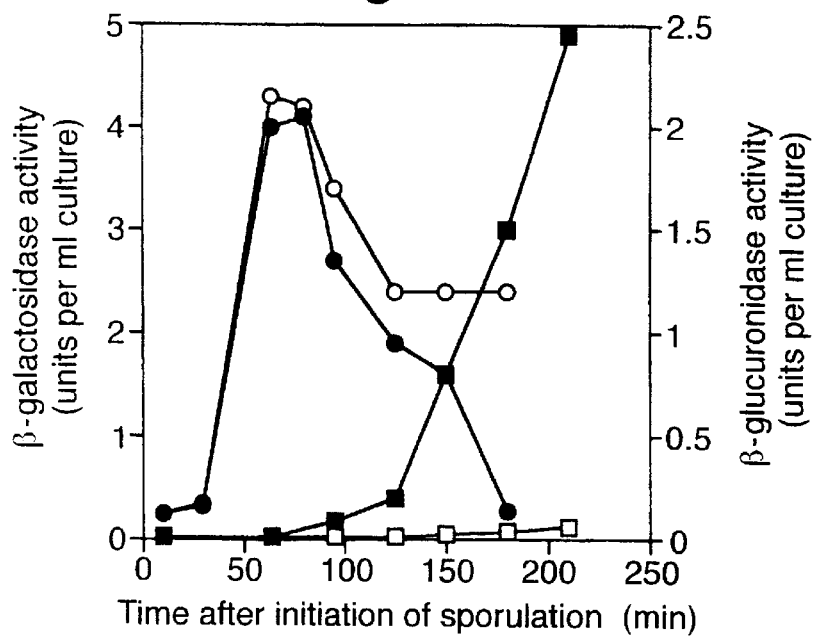
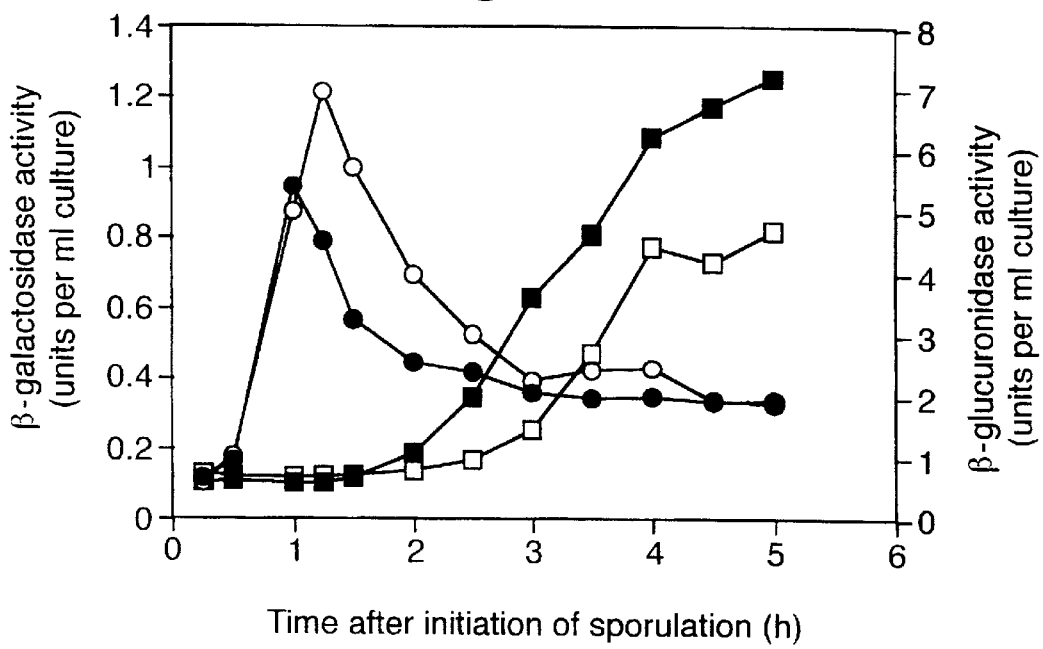

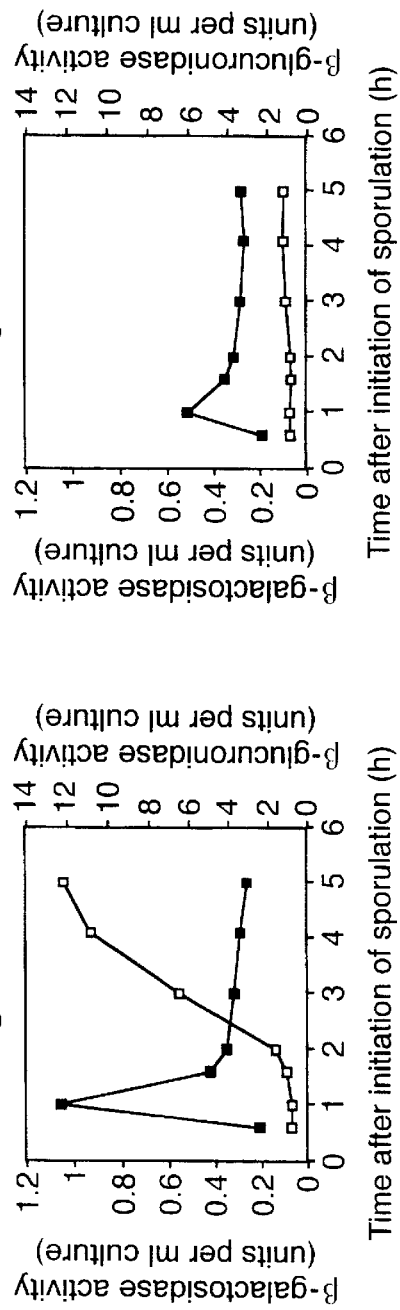
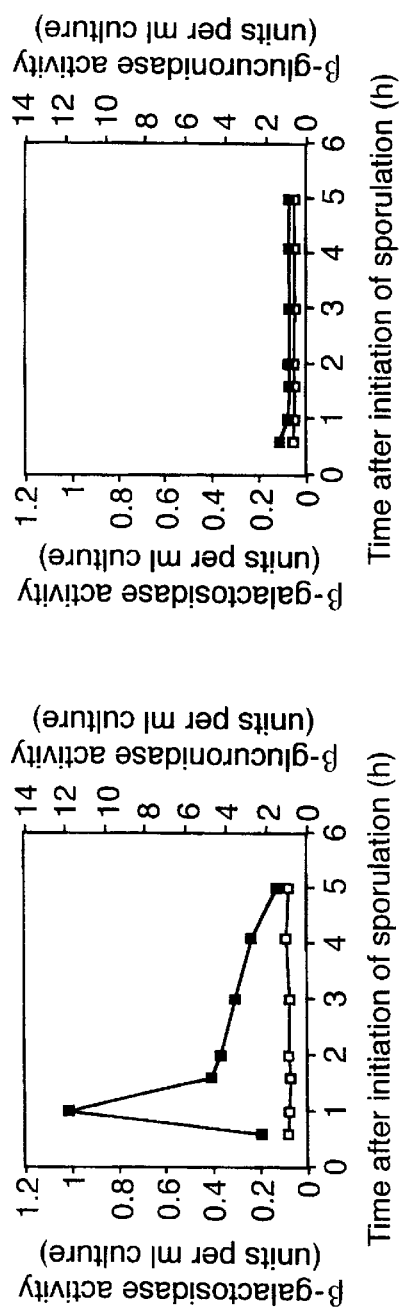

BACILLUS STRAIN AND ANTIBIOTIC SCREENING METHOD

The assay method described herein targets a group of related activities functioning in cell division. The assay is based on the observation that activation of the sporulation-specific transcription factor $\sigma^F$, which has been extensively studied in several laboratories (reviewed by Errington, 1996, *Trends in Genetics* 12, 31–34), requires the completion of cell division.

Synthesis of the sigma factor begins at the onset of sporulation but its product is initially held in an inactive state by the action of an anti-sigma factor, SpoIIAB. Release from inhibition requires the concerted action of at least two other proteins, SpoIIAA and SpoIIE, through a series of biochemical interactions that are now well characterised (Errington, 1996). These proteins serve to allow release of $\sigma^F$ activity only after the sporulating cell has undergone asymmetric cell division and to restrict the $\sigma^F$ activity to the smaller prespore cell type. This mechanism works in such a way that it renders $\sigma^F$ activation dependent on septation. Thus, mutants or genetically engineered strains of *B. subtilis* that are prevented from undergoing septation because of the absence of essential cell division gene products such as ftsZ (Beall and Lutkenhaus, 1991, *Genes Devel.* 5, 447–455), divIC (Levin and Losick, 1994, *J. Bacteriol.* 176, 716–722) or ftsL (Daniel, R. A. and Errington, J., unpublished results), synthesise but do not activate $\sigma^F$. The dependence of $\sigma^F$ activation on septation is herein used as the basis for a sensitive assay for inhibitors of cell division. Although the assay is based on inhibition of the specialised asymmetric cell division which occurs at the onset of sporulation, there is ample evidence that this process is functionally very similar to cell division in vegetative cells.

In one aspect the invention provides a Bacillus strain having a chromosome with two artificially introduced reporter genes, a first reporter gene having a promoter which is dependent on active $\sigma^F$ or $\sigma^E$ factors, and a second reporter gene which provides a measure of the synthesis of the (inactive) $\sigma^F$ or $\sigma^E$ factor.

In another aspect the invention provides a method of determining whether an agent inhibits cell division in Bacillus species, which method comprises inducing the Bacillus strain as described to sporulate in the presence of the agent, and observing expression of the first and second reporter genes. It is thought that the property of inhibiting cell division, is indicative of actual or potential anti-microbial properties in the agent. The method is thus expected to be useful for screening possible anti-microbial agents.

In another aspect the invention provides a method which comprises inducing the Bacillus strain as described to sporulate in the presence of an agent, observing expression of the first and second reporter genes and thereby determining that the agent inhibits cell division in the Bacillus species, and using the agent as an antibiotic to kill or inhibit the growth of bacteria.

The assay described below is based on use of $\sigma^F$ activation but it could also have used $\sigma^E$, another sporulation specific sigma factor that is dependent on asymmetric septation (Stragier et al, 1988, Cell, 52, 697–704). The dependence of $\sigma^E$ on septation is now thought to be an indirect effect caused by the dependence of $\sigma^E$ activity on $\sigma^F$ activation (see Errington, 1996). Use of an $\sigma^E$-dependent reporter gene would be less desirable as it would probably detect more non-specific inhibitors than with $\sigma^F$.

Any Bacillus species may be used that is capable of sporulating under suitable conditions and for which genetic constructions can be made. *B. subtilis* is conveniently accessible and well characterised and is preferred.

The Bacillus strain constructed has a chromosome with two reporter genes each linked to a different promoter. A reporter gene is one which on expression gives rise to an easily detected or observed phenotype. For example, the expressed protein may be an enzyme which acts on a substance to give a product that is easily observed e.g. because it is coloured or chemiluminescent or fluorescent. Reporter genes capable of being expressed in Bacillus species are well known and documented in the literature. The two reporter genes are preferably chosen so that their products can be readily assayed simultaneously. lacZ has been used for more than ten years with great success in *B. subtilis*. There are a range of useful substrates that generate coloured or fluorescent products upon hydrolysis by β-galactosidase. The uidA gene of *E. coli*, also known as the gusA gene, has recently been harnessed for similar purposes, and the range of substrates available for the gene product, β-glucuronidase, is similar to that of β-galactosidase.

In a preferred form, the assay uses a specific strain of *B. subtilis* containing two reporter genes. The first (gpr-uidA) provides a means of monitoring $\sigma^F$ (or $\sigma^E$) activity: its promoter is $\sigma^F$ (or $\sigma^E$)-dependent and it directs the production of an enzyme, β-glucuronidase, the activity of which can be readily measured by spectrophotometry or spectrofluorimetry. The second reporter gene (spoIIA-lacZ), which monitors expression of the gene encoding $\sigma^F$ (or $\sigma^E$), e.g. by virtue of having a promoter regulated similarly to the gene encoding sigma factor, provides a check for non-specific effects on sporulation or general inhibitors of gene expression. Again the product of the reporter gene is an enzyme, β-galactosidase, that can readily be measured. By using appropriate (enzyme) substrates, the two enzyme activities could be measured simultaneously.

To use the assay, this *B. subtilis* strain would be induced to sporulate by the resuspension method (Sterlini and Mandelstam, 1969, *Biochem. J.* 113, 29–37; Partridge and Errington, 1993, *Mol Microbiol* 8, 945–955). The culture would be dispensed into the wells of a microtitre plate just before the onset of asymmetric cell division (e.g. after 1 h at 37° C.). Individual wells would contain one or more potential inhibitors. After a period of incubation sufficient for induction of the spoIIA operon and activation of $\sigma^F$ (or $\sigma^E$), the microtitre plate cultures would be assayed for the two reporter activities by standard methods. Potential "hits" would show inhibition of β-glucuronidase activity but normal β-galactosidase activity (indicating synthesis but not activation of $\sigma^F$ (or $\sigma^E$))

Alternatively, test compounds can be dropped onto a lawn of sporulating cells on a solid surface (e.g. agar). In this case, the effect of the test compounds on reporter gene activity will be assessed by the colour or fluorescence produced by hydrolysis of colourigenic or fluorogenic substrates incorporated into the solid medium.

Two kinds of compounds might be expected to be detected by the assay. First, the desired compounds that inhibit asymmetric cell division. Second, compounds that interfere in some way with the protein—protein interactions, or the kinase or phosphatase activities known to be involved in $\sigma^F$ (or $\sigma^E$) regulation. These would be of purely academic interest (at least in the short term). The two classes could be readily distinguished by light microscopy because the latter class should form normal asymmetric septa.

Irrespective of the specific biomolecule affected in the screen, any compounds identified would be good potential candidates for development as antimicrobial agents because cell division is such a central target. Moreover, since cell division proteins tend to be highly conserved in bacteria, it is likely that broad spectrum inhibitors could be obtained.

Reference is directed to the accompanying drawings in which:

FIG. 1 is a graph showing the effect of depletion of FtsZ on expression of spoIIAA-lacZ and gpr-uidA;

FIGS. 2A–2D is a set of four graphs A, B, C, and D, showing detection of antibiotics affecting cell wall synthesis or cell division;

FIG. 3 is a graph showing use of 96 well microtitire plates to induce sporulation and reporter gene expression in a format suitable for high throughput screening.

The following examples illustrate the invention.

EXAMPLE 1

To illustrate the utility of the assay, a strain was constructed, containing the two reporter genes mentioned above (i.e., gpr-uidA and spoIIAA-lacZ) but in addition, a genetic insertion which renders the essential cell-division gene ftsZ dependent on an inducer chemical IPTG (Beall and Lutkenhaus, 1991). The strain was induced to sporulate under conditions in which the inducer was either present or absent and the two reporter activities were measured. FIG. 1 shows the effect of depletion of FtsZ on expression of spoIIAA-lacZ (circles) and gpr-uidA (squares). Filled symbols indicate the reporter enzyme activities in the presence of FtsZ, and open symbols, in the culture from which it was depleted by removal of the inducer, IPTG. As shown, in the presence of inducer, both reporter genes were strongly induced 1 to 2 h after the onset of sporulation, whereas in the absence of the inducer, resulting in inhibition of cell division, only the spoIIAA-lacZ reporter, producing β-galactosidase, was activated. Because $\sigma^F$ activity normally leads to repression of its own gene during sporulation, spoIIAA-lacZ expression is actually enhanced in the absence of active $\sigma^F$. Samples taken about 180 min after the initiation of sporulation and assayed for β-galactosidase and β-glucuronidase would thus readily detect specific inhibition of $\sigma^F$ activity. Note that in the absence of functional FtsZ, gpr-uidA activity is abolished (indicating that $\sigma^F$ does not become active), whereas spoIIAA-lacZ expression (leading to $\sigma^F$ synthesis) is enhanced, presumably because $\sigma^F$ activity normally leads to repression of its own gene later in sporulation.

EXAMPLE 2

To show that the assay method could detect actual inhibitors of cell division, the experiments shown in FIG. 2 were performed. The bacterial strain used (846) carried the following genetic markers: trpC2 Ω(amyE::gpr-uidA aphA-3) (φ105J19) spoIIAA-lacZ cat. Thus, β-galactosidase (from the lacZ gene) provides an indication of $\sigma^F$ synthesis and β-glucuronidase (from the uidA gene) a measure of $\sigma^F$ activation (dependent on cell division). The strain was induced to sporulate by standard methods (Partridge and Errington, 1993, Mol. Microbiol. 8, 945–955). Immediately after induction, the culture was divided into several portions, which were treated with different known antibiotics. In the control (untreated) culture (panel A), β-galactosidase (filled squares) and β-glucuronidase (open squares) activities produced from the two reporter genes followed their normal kinetics (Errington and Mandelstam, 1986, J. Gen. Microbiol. 132, 2967–2976; Partridge and Errington, 1993) (see also FIG. 1). In the presence of antibiotics that affect cell wall synthesis or cell division (bacitracin [50 μg/ml; panel B] and carbenicillin [110 μg/ml; panel C]) $\sigma^F$ synthesis occurred, as indicated by accumulation of β-galactosidase with near normal kinetics, but its activation was blocked, as indicated by the elimination of β-glucuronidase activity. In contrast, with a general inhibitor of protein synthesis, erythromycin (50 μg/ml), both reporter genes were blocked (panel D).

Note that in the case of bacitracin (and vancomycin; data not shown), which affects cell wall synthesis generally, addition of the inhibitor at the concentration indicated caused a slight reduction in expression of the spoIIAA-lacZ reporter (as well as a block in gpr-uidA expression). It is likely that such a reduction in expression would not occur with inhibitors of proteins required specifically for formation of the septum, though no such inhibitors are presently available. Thus, of test chemicals that block gpr-uidA expression, those giving the highest levels of spoIIAA-lacZ expression would be most likely to affect targets required specifically for septation. Nevertheless, compounds giving a partial reduction in spoIIAA-lacZ expression might still be of commercial interest, as functions involved in cell wall synthesis are likely, in general, to provide the necessary selective toxicity needed for good antibiotics.

Note also that in the case of carbenicillin, cell lysis, as indicated by a fall in culture optical density ($OD_{600}$), began about 2 to 3 hours after the initiation of sporulation. Although this lysis probably occurs too late to explain the large difference in reporter activity, it provides an indication of a possible source of "false positive" results that might arise when the assay is put into practice. Since the gpr-uidA reporter is turned on about 1 hour later than the spoIIAA-lacZ reporter, it is possible that agents causing slow killing of the cells would have differential effects on expression of the earlier and later reporter genes. Agents having this effect through cell lysis could be detected and excluded, if necessary, by measuring the optical density of the culture about 3 or 4 hours after initiation of sporulation.

EXAMPLE 3

To confirm that the results obtained above with batch grown B. subtilis strains could be obtained for cells grown in a microtitre plate format, cells of strain 846 (see above) were induced to sporulate by the normal method involving resuspension in a starvation medium (Partridge and Errington, 1993). Immediately after resuspension, the culture was divided into two portions. One portion was allowed to continue sporulating in the glass flask, as usual (filled symbols in FIG. 3). The other half of the culture was dispensed, in 50 μl aliquots, into the wells of a standard 8 by 12 microtitre plate with 360 μl wells (open symbols). The microtitre plate was incubated alongside the glass flask, shaking at 37° C. At intervals, the contents of one well of the plate and 50 μl of the flask culture were removed and assayed for β-galactosidase (circles) and β-glucuronidase (squares). As shown in FIG. 3, the time courses showed good induction of both reporter enzymes in the microtitre plate sporulated culture, though there were minor qualitative differences in their time courses from those of the flask culture. Cells induced to sporulate in microtitre plates were also observed to form spores with similar efficiency to those in flasks. We conclude that the sporulation experiments required for the assay to be run in high throughput mode can be done in readily available microtitre plates.

What is claimed is:

1. A Bacillus strain having a chromosome with two artificially introduced reporter genes, a first reporter gene having a promoter which is dependent on active $\sigma^F$ or $\sigma^E$ factors, and a second reporter gene whose promoter is regulated similarly to the promoter of the gene encoding $\sigma^F$ or $\sigma^E$ factor.

2. A Bacillus strain as claimed in claim 1, wherein the promoter of the first reporter gene is that of the gpr gene and the promoter of the second reporter gene is that of the spoIIAA gene.

3. A Bacillus strain as claimed in claim 1, wherein the reporter genes are lacZ and uidA.

4. A Bacillus strain as claimed in claim 1, which is a *B. subtilis* strain.

5. A method of determining whether an agent inhibits cell division in Bacillus species, which method comprises inducing the Bacillus strain of claim 1 to divide asymmetrically in the presence of the agent, and observing expression of the first and second reporter genes, wherein expression of the second reporter gene but not the first reporter gene indicates that the agent inhibits cell division.

6. The method of claim 5 wherein asymmetric division is induced by inducing sporulation.

7. A method as claimed in claim 5, wherein the two reporter genes are expressed as enzymes, the activities of which are observed by fluorimetry or spectrophotometry.

8. A method as claimed in claim 5, wherein the Bacillus strain is induced to sporulate and is contacted, just prior to asymmetric cell division, with the agent.

9. A method as claimed in claim 5, wherein, in a case where expression of the first reporter gene is observed to be reduced relative to the second reporter gene, the cells are examined to determine whether normal asymmetric septa have formed.

10. A method which comprises:

inducing the Bacillus strain of claim 1 to sporulate in the presence of an agent;

observing expression of the first and second reporter genes, wherein expression of the second reporter gene but not the first reporter gene indicates that the agent inhibits cell division in the Bacillus species; and using the agent identified as inhibiting cell division as an antibiotic to kill or inhibit cell division of bacteria.

* * * * *